(12) United States Patent
Mage

(10) Patent No.: US 6,715,157 B2
(45) Date of Patent: Apr. 6, 2004

(54) SPORTS GOGGLES

(75) Inventor: Jerome Jacques Marie Mage, Beverly Hills, CA (US)

(73) Assignee: Spy Optic, Inc., Carlsbad, CA (US)

( * ) Notice: Subject to any disclaimer, the term of this patent is extended or adjusted under 35 U.S.C. 154(b) by 0 days.

(21) Appl. No.: 10/224,097

(22) Filed: Aug. 20, 2002

(65) Prior Publication Data

US 2004/0034904 A1 Feb. 26, 2004

(51) Int. Cl.⁷ .................................................. A61F 9/02
(52) U.S. Cl. ............................................... 2/439; 2/426
(58) Field of Search .......................... 2/426, 421, 425, 2/12, 13, 10, 429, 439, 440, 442, 443, 450, 452

(56) References Cited

U.S. PATENT DOCUMENTS

| | | |
|---|---|---|
| 2,042,400 A | 5/1936 | Hon |
| D118,391 S | 1/1940 | Sanders |
| D134,290 S | 11/1942 | Ditto |
| D148,974 S | 3/1948 | Bolle |
| D151,693 S | 11/1948 | Jacobson |
| D169,724 S | 6/1953 | Bauer et al. |
| D170,435 S | 9/1953 | Weissman |
| 2,778,270 A | 1/1957 | Pomerance |
| D189,436 S | 12/1960 | Carmichael |
| 3,015,987 A | 1/1962 | Harrison |
| D192,884 S | 5/1962 | Petitto |
| D200,355 S | 2/1965 | Angelis |
| D201,578 S | 7/1965 | Petitto |
| D204,100 S | 3/1966 | Shindler |
| D204,210 S | 3/1966 | McCulloch |
| D204,636 S | 5/1966 | Radziwon et al. |
| D204,959 S | 5/1966 | McCulloch |
| D205,093 S | 6/1966 | Gaboriault |
| 3,298,031 A | 1/1967 | Morgan |
| D210,422 S | 3/1968 | Mitchell |
| D212,392 S | 10/1968 | Mitchell |
| D215,761 S | 10/1969 | Mitchell |
| D218,569 S | 9/1970 | McCracken |
| D218,953 S | 10/1970 | Maiese |
| D227,407 S | 6/1973 | Marchi |

(List continued on next page.)

FOREIGN PATENT DOCUMENTS

GB 2 165 138 * 4/1986 ............ A42B/3/00

OTHER PUBLICATIONS

"Spectacles", Oct. 1985, p. 55.
"Accessories", Dec. 1985, p. 48.

(List continued on next page.)

Primary Examiner—Gary L. Welch
(74) Attorney, Agent, or Firm—Stetina Brunda Garred & Brucker

(57) ABSTRACT

A pair of sports goggles is disclosed. The sports goggles include: a lens a flexible frame housing the lens, and a headband. The goggles also include rotatable headband mounting members and/or a removable/replaceable moisture wicking system affixed to the inner surface of the frame. The lens is configured to be positioned over a wearer's eyes. The flexible frame housing houses the lens and is defined by a frame top, a frame bottom, a frame right side and a frame left side. The frame has an inner surface that is worn towards the wearer's face. The headband has a headband left end and a headband right end. The first and second rotatable headband mounting members are attached to the headband left end and the headband right end respectively and the first and second rotatable headband mounting members are attached to the frame left side and the frame right side respectively for providing rotatable engagement of the headband with the frame.

12 Claims, 3 Drawing Sheets

U.S. PATENT DOCUMENTS

| | | |
|---|---|---|
| D231,260 S | 4/1974 | Jelinek |
| D245,083 S | 7/1977 | Zimmermann |
| D246,718 S | 12/1977 | Zimmermann |
| D246,791 S | 12/1977 | Shindler |
| 4,240,718 A | 12/1980 | Wichers et al. |
| 4,391,498 A | 7/1983 | Rengstorff |
| 4,447,914 A | 5/1984 | Jannard |
| 4,515,448 A | 5/1985 | Tackles |
| 4,556,995 A | 12/1985 | Yamamoto |
| 4,571,748 A | 2/1986 | Carroll et al. |
| D289,301 S | 4/1987 | Jannard |
| 4,665,598 A | 5/1987 | Murai et al. |
| 4,689,838 A | 9/1987 | Angermann et al. |
| 4,707,863 A | 11/1987 | McNeal |
| D293,450 S | 12/1987 | Jannard |
| 4,716,601 A | 1/1988 | McNeal |
| 4,730,915 A | 3/1988 | Jannard |
| D295,869 S | 5/1988 | Lamy |
| 4,826,309 A | 5/1989 | VanNeste |
| 4,859,048 A | 8/1989 | Jannard |
| 4,867,550 A | 9/1989 | Jannard |
| 4,918,753 A * | 4/1990 | Mermillod ........................ 2/10 |
| D311,197 S | 10/1990 | Jannard |
| 4,978,209 A | 12/1990 | Ohba |
| 4,989,274 A | 2/1991 | Patelski, III |
| D320,402 S | 10/1991 | Jannard et al. |
| 5,054,903 A | 10/1991 | Jannard et al. |
| 5,056,163 A * | 10/1991 | Chou ........................... 2/453 |
| D323,333 S | 1/1992 | Jannard et al. |
| D323,516 S | 1/1992 | Miklitarian |
| D324,058 S | 2/1992 | Longsdorf et al. |
| D324,394 S | 3/1992 | Jannard |
| D324,528 S | 3/1992 | Jannard |
| D325,040 S | 3/1992 | Jannard |
| D326,674 S | 6/1992 | Mehringer |
| D328,468 S | 8/1992 | Jannard |
| 5,137,342 A | 8/1992 | Jannard et al. |
| D329,442 S | 9/1992 | Jannard |
| D329,445 S | 9/1992 | Jannard |
| D330,035 S | 10/1992 | Jannard |
| D330,716 S | 11/1992 | Jannard |
| D330,903 S | 11/1992 | Jannard |
| D331,587 S | 12/1992 | Jannard et al. |
| D331,763 S | 12/1992 | Jannard |
| D333,145 S | 2/1993 | Jannard |
| 5,182,817 A | 2/1993 | Branum |
| D334,758 S | 4/1993 | Reymondet et al. |
| D335,887 S | 5/1993 | Jannard |
| 5,208,614 A | 5/1993 | Jannard |
| D336,908 S | 6/1993 | Jannard |
| D339,816 S | 9/1993 | Jackson |
| 5,249,001 A | 9/1993 | Jannard |
| D342,534 S | 12/1993 | Jannard et al. |
| D342,959 S | 1/1994 | Jannard et al. |
| D343,182 S | 1/1994 | Jannard |
| D344,281 S | 2/1994 | Jannard et al. |
| D344,282 S | 2/1994 | Hirschman |
| D344,742 S | 3/1994 | Jannard |
| 5,303,428 A | 4/1994 | Pernicka |
| D347,014 S | 5/1994 | Arnette |
| 5,339,119 A | 8/1994 | Gardner |
| 5,341,516 A | 8/1994 | Keim |
| 5,363,512 A | 11/1994 | Grabos et al. |
| D358,159 S | 5/1995 | Lai |
| 5,410,763 A | 5/1995 | Bolle |
| 5,421,037 A | 6/1995 | Schulze |
| D362,260 S | 9/1995 | Lin |
| D363,504 S | 10/1995 | Arnette |
| D365,591 S | 12/1995 | Jannard et al. |
| D366,666 S | 1/1996 | Arnette |
| D366,890 S | 2/1996 | Arnette |
| D366,891 S | 2/1996 | Arnette |
| D368,108 S | 3/1996 | Lei |
| 5,495,623 A | 3/1996 | Leonardi |
| D369,375 S | 4/1996 | Jannard et al. |
| 5,511,251 A | 4/1996 | Brakas |
| 5,541,674 A | 7/1996 | Jannard |
| D373,781 S | 9/1996 | Simioni et al. |
| 5,553,326 A * | 9/1996 | Moore ........................... 2/181 |
| D376,810 S | 12/1996 | Ohie |
| 5,583,583 A | 12/1996 | Wilson |
| 5,594,511 A | 1/1997 | Lin |
| 5,602,603 A | 2/1997 | Bondet |
| 5,610,668 A | 3/1997 | Mage |
| 5,611,644 A * | 3/1997 | Lutz ........................... 405/186 |
| 5,642,178 A | 6/1997 | Leonardi et al. |
| D380,766 S | 7/1997 | Simioni |
| D381,674 S | 7/1997 | Bernheiser |
| 5,648,832 A | 7/1997 | Houston |
| 5,682,621 A | 11/1997 | Park |
| 5,689,834 A | 11/1997 | Wilson |
| 5,752,280 A * | 5/1998 | Hill ............................... 2/453 |
| 5,765,223 A * | 6/1998 | McCausland ...................... 2/9 |
| 5,790,982 A * | 8/1998 | Boutboul et al. ................. 2/53 |
| 5,802,622 A | 9/1998 | Baharad et al. |
| 5,890,237 A | 4/1999 | Herman |
| 5,898,468 A | 4/1999 | Mage |
| 5,987,652 A * | 11/1999 | Fowler ........................... 2/424 |
| 6,047,410 A | 4/2000 | Dondero |
| 6,065,833 A | 5/2000 | Tiano |
| 6,092,895 A | 7/2000 | Sato et al. |
| 6,094,751 A * | 8/2000 | Parks ........................... 2/431 |
| 6,098,204 A | 8/2000 | Arnette |
| 6,105,177 A | 8/2000 | Paulson et al. |
| 6,138,285 A | 10/2000 | Robrahn et al. |
| 6,253,387 B1 | 7/2001 | Yu |
| 6,276,795 B1 | 8/2001 | Hall et al. |
| 6,341,863 B1 | 1/2002 | Lieh |
| 6,477,717 B1 * | 11/2002 | Winefordner et al. ......... 2/428 |

OTHER PUBLICATIONS

"Clinton Optical Co., Inc.", p. 28.
"Optical Journal & Review of Optometry", Apr. 1969, p. 17.
"Optical Journal & Review of Optometry", Sep. 1971, p. 36.
"Guild Guide", Sep. 1972, p. 9.
"Optometric Weekly", Dec. 1972, p. 7.
"Luminos Catalog", Mar. 1973, p. 4.
"Optometric Weekly", Jun. 1974, p. 23.
"The Optician", Sep. 1977, p. 8.
"Lunettes de Soleil", Apr.1983, p. 4.
"Accessories", Dec. 1986, front cover.
"Spectacle Frames & Optical Accessories Speck", Mar. 1987, p. 188.
"Optician", Apr. 1987, p. 2.
"Optician", Apr. 1987.
"Optician", May 1988.
"Vogue", May 1992.
"Macys Catalog", Jul. 1996, p. 32.

* cited by examiner

SPORTS GOGGLES

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

The present invention relates generally to goggles and more particularly to a pair of sports goggles having a headband attached with rotatable mounting members and a removable/replaceable wicking moisture system.

Goggles may be worn by participants in a variety of sports, such as motorcycle racing, skiing, etc. It is often desirable to wear a helmet at the same time that the goggles are worn. The wearer typically places the head band of the goggles on the outside of the helmet so that the goggles can be adjusted if necessary. Prior art goggles are not designed to be worn with a helmet. Prior art goggles do not fit well over a helmet and are difficult to adjust.

Thus, there is a need for a pair of sports goggles that fit properly over a helmet and allow the user to adjust the goggles about the helmet.

Another problem with prior art sports goggles is that wearers tend to perspire. The perspiration may get in the wearer's eyes. Typically, goggles include a foam which may absorb some of the perspiration. However, the foam can not be washed and becomes dirty and smelly. Additionally, the foam may deteriorate and become uncomfortable. For example, it may become hard and scratchy.

Thus, there is also a need for sports goggles that can absorb perspiration during use, including a method for removing/replacing the moisture absorber when desired.

BRIEF SUMMARY OF THE INVENTION

An aspect of the invention may be regarded as a pair of goggles having a lens, a flexible frame housing the lens, a headband, and rotatable headband mounting members. The lens is configured to be positioned over a wearer's eyes. The flexible frame housing houses the lens and is defined by a frame top, a frame bottom, a frame right side and a frame left side. The frame has an inner surface that is worn towards the wearer's face. The headband has a headband left end and a headband right end. First and second rotatable headband mounting members are attached to the headband left end and the headband right end respectively and the first and second rotatable headband mounting members are attached to the frame left side and the frame right side respectively for providing rotatable engagement of the headband with the frame.

The rotatable headband mounting members rotate about an x-axis and a y-axis.

The rotatable headband mounting members may each comprise a swivel pin member and a clip, wherein a first clip is attached to the headband left end and a first swivel pin member attaches the first clip to the frame left side and a second clip is attached to the headband right end and a second swivel pin member attaches the second clip to the frame right side. The clip may include a logo member.

The pair of goggles may include a removable/replaceable moisture wicking system affixed to the inner surface of the frame. The moisture wicking system may include a first layer of a removable material affixed to the inner surface of the frame and a second layer of a highly absorbent material affixed to the first layer. The first layer may be a removable moisture absorbing foam material. The moisture wicking system may be affixed to the inner surface of the frame using a peel-away adhesive.

BRIEF DESCRIPTION OF THE DRAWINGS

These as well as other features of the present invention will become more apparent upon reference to the drawings wherein.

DETAILED DESCRIPTION OF THE INVENTION

Figure 1:
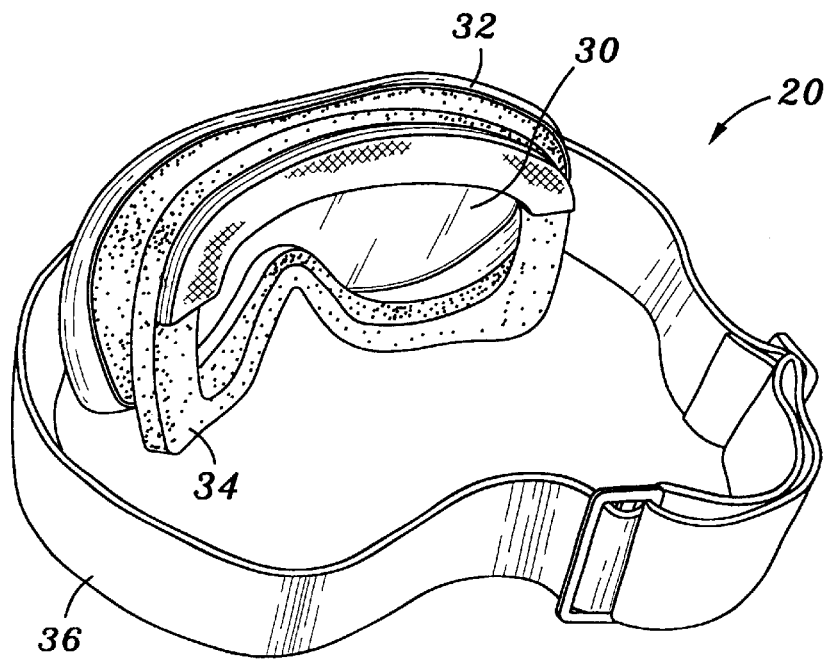
FIG. 1 is a rear perspective view of a pair of sports goggles having a removable/replaceable moisture wicking system affixed to an inner surface of the goggles frame.

Referring now to the drawings wherein the showings are for purposes of illustrating preferred embodiments of the present invention only, and not for purposes of limiting the same, FIG. 1 illustrates a pair of sports goggles 20 formed in accordance with the present invention. The goggles include rotatable headband mounting members 40 that are ideally suited to allow the goggles to be worn with a helmet. The rotatable headband mounting members 40 allow the headband to be comfortably worn over the helmet while allowing for easy adjustability. The rotatable headband mounting members 40 are described in further detail later. The goggles 20 also include a removable/replaceable moisture wicking system 34 as described in further detail next.

As shown in FIG. 1, the sports goggles 20 include a lens 30. The lens 30 is housed in a flexible frame 32 which includes an inner surface that is placed against the wearer's face. The top of the inner surface is worn against the wearer's forehead and the bottom of the inner surface contacts the wearer below the eyes (e.g., proximate the cheekbones) and across the wearer's nose (at about the bridge of the nose). A portion or all of the inner surface of the frame 32 is lined, for example with a foam liner. Such liners provide for a better fit and greater comfort for the wearer.

Figure 2:
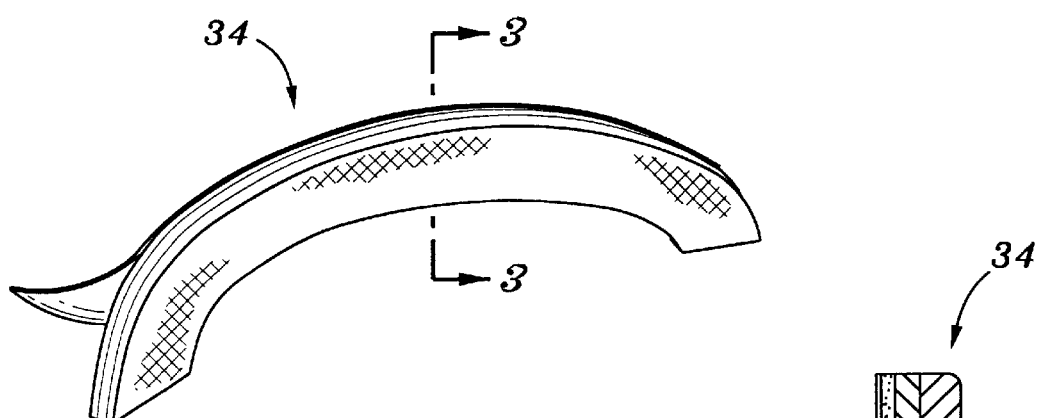
FIG. 2 illustrates the removable/replaceable moisture wicking system of the sports goggles shown in FIG. 1.
Figure 3:
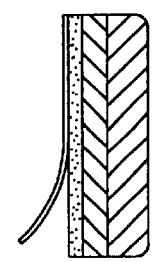
FIG. 3 is a cross sectional view of the removable/replaceable moisture wicking system shown in FIG. 2.

Wearers of sports goggles 20 often sweat. Padding or liners of prior art goggles do not sufficiently absorb water or perspiration. The goggles 20 of the present invention include an absorbent removable/replaceable moisture wicking system 34, such as the one shown in FIGS. 2 and 3. The moisture wicking system 34 is applied to the inner surface of the frame 32 using a peel-away adhesive. A removable material, such as a moisture absorbing foam is attached as a first layer to the inner surface of the goggles frame 32. A second layer which is a super absorbent layer of material is adhered to the first layer. In exemplary embodiments, the moisture wicking system 34 is attached to the upper portion of the inner surface of the frame 32, i.e., across the wearer's forehead. It will be appreciated that the moisture wicking system 34 could be placed around the entire perimeter of the inner surface of the frame 32 of the goggles 20. As shown in FIGS. 2 and 3, the upper layer can be removed. The upper (second) layer can then be replaced by adhering a new second layer with a peel away adhesive. For example, double-sided tape can be used to adhere the second layer to the first layer.

Figure 4:
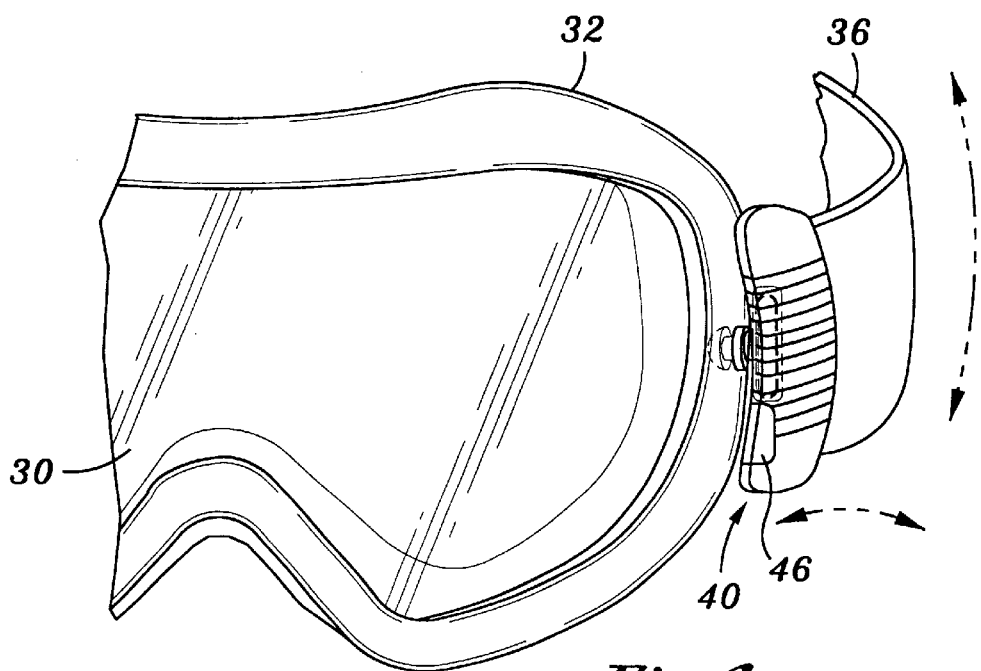
FIG. 4 is a perspective view showing a rotatable headband mounting member mounted to the sports goggles shown in FIG. 1.
Figure 5:
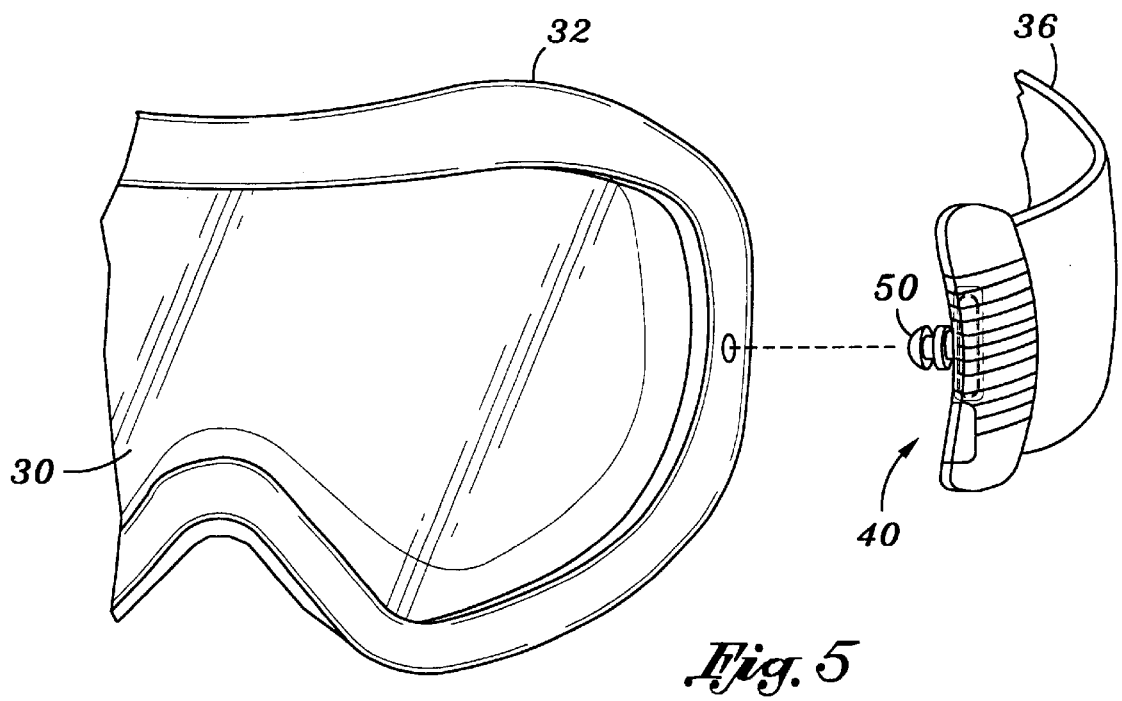
FIG. 5 is a perspective view showing the rotatable headband mounting member of FIG. 4 not mounted to the sports goggles.

As mentioned above, the sports goggles 20 of the present invention include rotatable headband mounting members 40. The mounting members 40 rotatably connect the headband 36 to the frame 32. As shown in FIG. 4, the rotatable mounting members 40 allow the headband 36 to be rotated about an x-axis and a y-axis.

Figure 6:
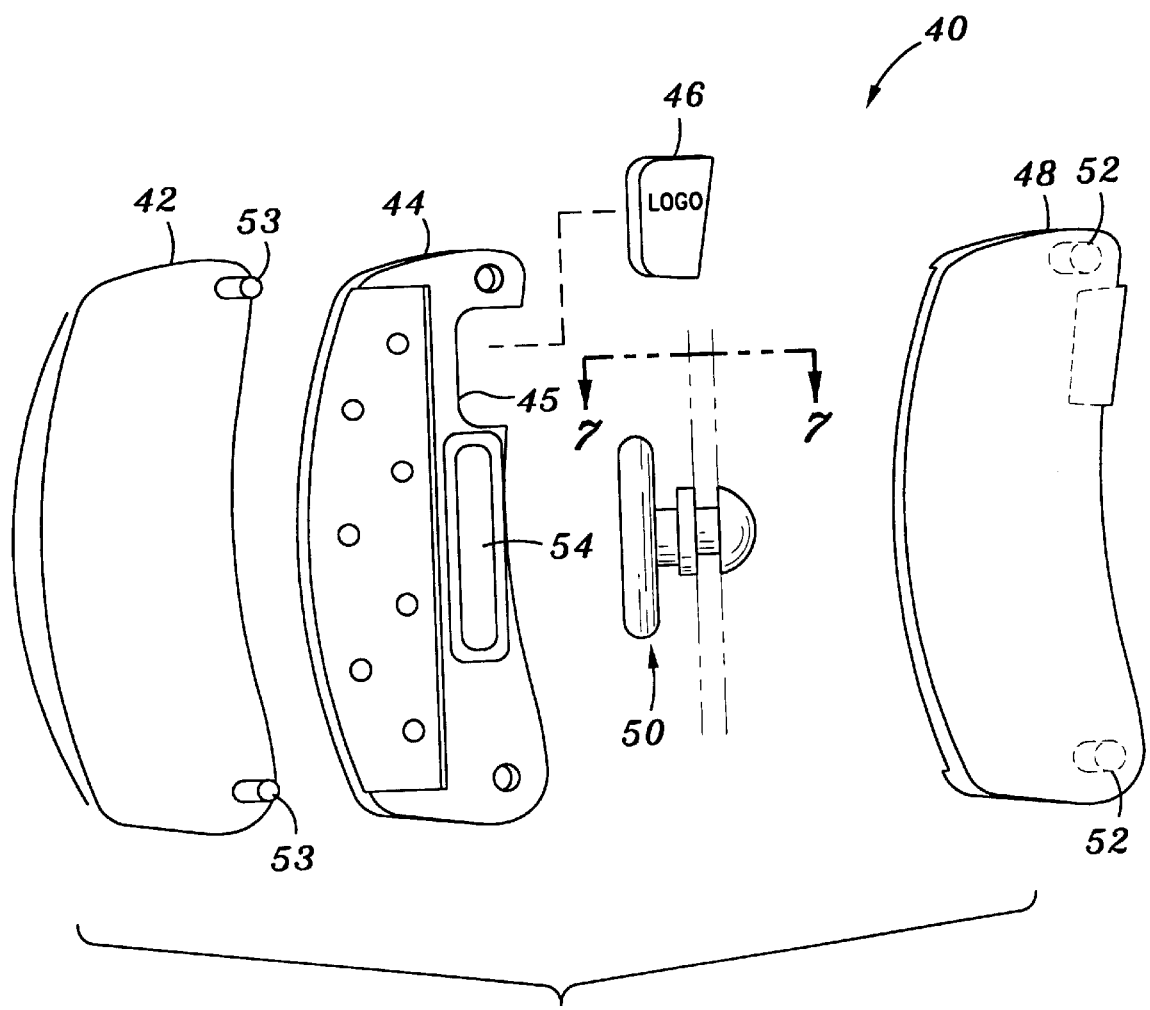
FIG. 6 is a cutaway view of the rotatable mounting member shown in FIG. 5.
Figure 7:
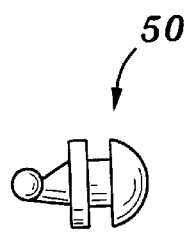
FIG. 7 is a perspective view of a swivel pin member that is used to rotatably connect the rotatable headband mounting member to the sports goggles.

FIG. 6 is an exploded view of an exemplary embodiment of the rotatable headband mounting member 40 which includes a center piece 44 that may include a logo. The center piece includes an aperture 54 through which a swivel connector member 50 is placed. The swivel connector member 50 allows the headband to rotate. Preferably, the swivel connector member 50 allows the rotatable headband mounting members 40 to rotate about multiple axes as shown in FIG. 4.

In the embodiment shown, a logo is on a logo member 46 that is configured to fit into a recess 45 in the middle piece 44. The logo member 46 wraps around the front outer side 48 so that the logo can be seen as shown in FIG. 4. The swivel connector member 50 and logo member 46 are secured in place when the front outer side 48 and the rear outer side 42 are connected. In the embodiment shown, the front outer side 48 and the rear outer side 42 are snapped together by inserting projections 53 (on the rear outer,side 42) into recesses 52 (on the front outer side 48).

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A pair of goggles configured to be worn with a helmet, the goggles comprising:
   a lens configured to be positioned over a wearer's eyes;
   a flexible frame housing the lens, the frame defined by a frame top, a frame bottom, a frame right side and a frame left side, the frame having an inner surface that is worn towards the wearer's face;
   a headband having a headband left end and a headband right end and configured to be worn over the helmet; and
   first and second rotatable headband mounting members attached to the headband left end and the headband right end respectively, the first and second rotatable headband mounting members attached to the frame left side and the frame right side respectively for providing rotatable engagement of the headband with the frame such that the goggles can be adjusted about the helmet.

2. The pair of goggles in claim 1, wherein the rotatable headband mounting members each comprise a swivel pin member and a clip, wherein a first clip is attached to the headband left end and a first swivel pin member attaches the first clip to the frame left side and a second clip is attached to the headband right end and a second swivel pin member attaches the second clip to the frame right side.

3. The pair of goggles in claim 2, wherein the clip comprises a logo member.

4. The pair of goggles of claim 1, further comprising a removable/replaceable moisture wicking system affixed to the inner surface of the frame.

5. The pair of goggles of claim 4, wherein the moisture wicking system comprises a first layer of a removable material affixed to the inner surface of the frame and a second layer of a highly absorbent material affixed to the first layer.

6. The pair of goggles of claim 5, wherein the first layer is a removable moisture absorbing foam material.

7. The pair of goggles of claim 5, wherein the moisture wicking system is affixed to the inner surface of the frame using a peel-away adhesive.

8. A pair of goggles, comprising:
   a lens configured to be positioned over a wearer's eyes;
   a flexible frame housing the lens, the flexible frame having an inner surface that is worn towards the wearer's face;
   a headband having a headband left end and a headband right end;
   first and second headband mounting members attached to the headband left end and the headband right end respectively; and
   a removable/replaceable moisture wicking system affixed to the inner surface of the frame using a peel-away adhesive, the removable/replaceable moisture wicking system having a first layer of a moisture absorbing material affixed to the inner surface of the frame and a second removable layer of a highly absorbent material affixed to the first layer using a peel-away adhesive.

9. The pair of goggles of claim 8, wherein the first layer is a removable moisture absorbing foam material.

10. The pair of goggles of claim 8, wherein the first and second headband mounting members are rotatable and are attached to the headband left end and the headband right end respectively, the first and second headband mounting members attached to the frame left side and the frame right side respectively or providing rotatable engagement of the headband with the frame.

11. The pair of goggles in claim 10, wherein the headband mounting members each comprise a swivel pin member and a clip, wherein a first clip is attached to the headband left end and a first swivel pin-member attaches the first clip to the frame left side and a second clip is attached to the headband right end and a second swivel pin member attaches the second clip to the frame right side.

12. The pair of goggles in claim 11, wherein the clip comprises a logo member.

* * * * *